United States Patent
Schena

(10) Patent No.: US 9,850,994 B2
(45) Date of Patent: *Dec. 26, 2017

(54) COMPACT CABLE TENSION TENDER DEVICE

(75) Inventor: Bruce M. Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1254 days.

This patent is subject to a terminal disclaimer.

(21) Appl. No.: 12/766,794

(22) Filed: Apr. 23, 2010

(65) Prior Publication Data

US 2010/0219388 A1    Sep. 2, 2010

Related U.S. Application Data

(63) Continuation of application No. 11/549,087, filed on Oct. 12, 2006, now Pat. No. 7,736,254.

(51) Int. Cl.
*F16H 19/06* (2006.01)
*B25J 9/10* (2006.01)
*A61B 19/00* (2006.01)
*A61B 34/00* (2016.01)
*A61B 34/30* (2016.01)

(52) U.S. Cl.
CPC ............. *F16H 19/06* (2013.01); *A61B 34/30* (2016.02); *A61B 34/71* (2016.02); *B25J 9/1045* (2013.01); *F16H 19/0672* (2013.01); *A61B 2034/715* (2016.02)

(58) Field of Classification Search
USPC ............. 74/89.22, 89.2, 501.5 R, 500.5, 74/502.4–502.6, 506; 474/101, 109, 112, 474/115, 117; 242/388–388.8, 155 R, 242/155 BW, 390–393; 254/277; 49/332, 382, 348, 349, 374, 138, 139
See application file for complete search history.

(56) References Cited

U.S. PATENT DOCUMENTS

| | | | |
|---|---|---|---|
| 2,212,823 A | | 8/1940 | Bulk |
| 2,810,300 A | * | 10/1957 | Pigford .................... 74/501.5 R |
| 2,992,568 A | * | 7/1961 | Benkovsky et al. ..... 74/501.5 R |
| 3,180,176 A | * | 4/1965 | De Maagd et al. ..... 74/501.5 R |
| 3,266,335 A | | 8/1966 | Wright, Jr. |

(Continued)

OTHER PUBLICATIONS

PCT/US07/91183 International Search Report, dated Jun. 19, 2008, 3 pages.

(Continued)

*Primary Examiner* — Daniel D Yabut
(74) *Attorney, Agent, or Firm* — Blakely Sokoloff Taylor & Zafman LLP

(57) ABSTRACT

A compact cable tension tender device includes first and second pulleys rotatably coupled to a drive shaft. First and second plates are fixed to the drive shaft. Drive stops on the plates engage and rotate the pulleys when the drive shaft is rotated. A resilient coupler urges the first and second pulleys to rotate away from engagement with the drive stops. Cables are coupled to the pulleys and adjusted to be in tension such that the first and second pulleys both engage the drive stops at the same time. The engagement of both pulleys with the drive stops at the same time minimizes lost motion when reversing the rotation of the drive shaft.

13 Claims, 7 Drawing Sheets

(56) References Cited

U.S. PATENT DOCUMENTS

| | | | | |
|---|---|---|---|---|
| 3,433,089 | A | * | 3/1969 | Geyer ..................... 74/501.5 R |
| 3,712,147 | A | | 1/1973 | Bernstein |
| 4,529,155 | A | * | 7/1985 | Bramwell ................ 74/501.5 R |
| 4,936,159 | A | * | 6/1990 | Kallio ..................... 74/501.5 R |
| 4,938,304 | A | * | 7/1990 | Yamaguchi ............. 74/501.5 R |
| 5,365,802 | A | * | 11/1994 | Suzuki et al. .............. 74/500.5 |
| 5,813,282 | A | * | 9/1998 | Azuma ......................... 74/506 |
| 6,193,621 | B1 | | 2/2001 | McClosky |
| 7,025,298 | B2 | * | 4/2006 | Priest ........................ 242/388.8 |
| 7,736,254 | B2 | * | 6/2010 | Schena ........................ 474/101 |
| 2004/0065018 | A1 | | 4/2004 | Regnier et al. |

OTHER PUBLICATIONS

PCT/US07/81183 Written Opinion of the International Search Authority, dated Jun. 19, 2008, 8 pages.
William Townsend of Barrett Technology, Inc. for Johnson Space Center, Improved Cable-Drive Pretensioner, Jul. 2000, http://www.nasatech.com/briefs/july00/msc22405.
Vertut, Jean and Coeffet, Philippe Coiffet, "Robot Technology; Volume 3A Teleoperation and Robotics Evolution and Development", 1986, Prentice-Hall Inc.

* cited by examiner

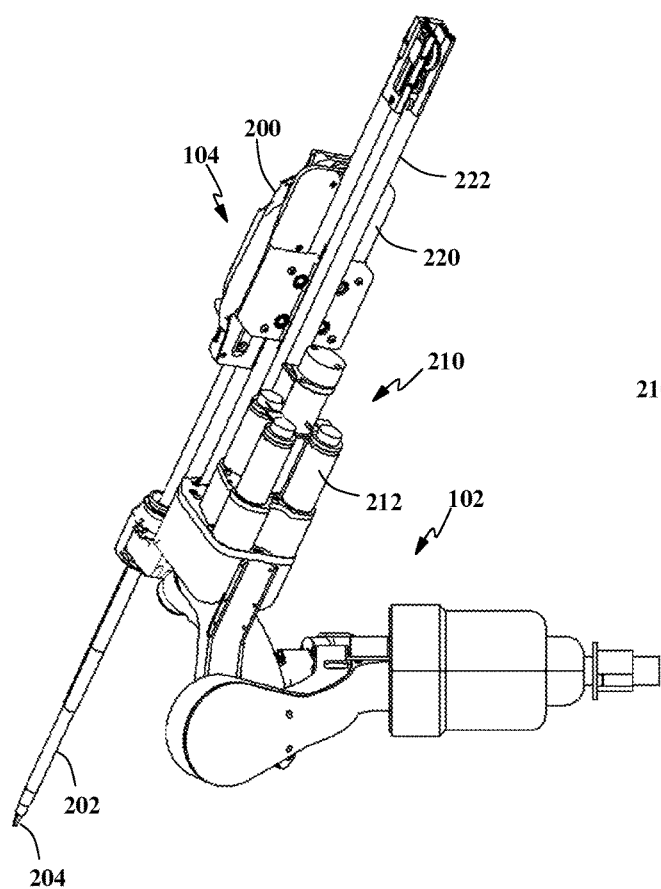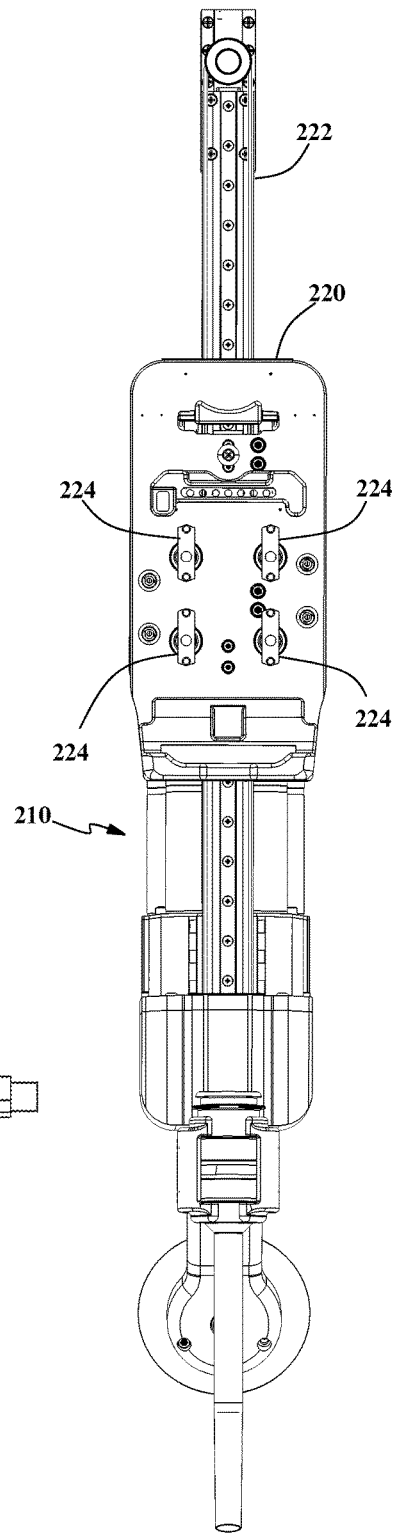
FIG. 1
FIG. 2

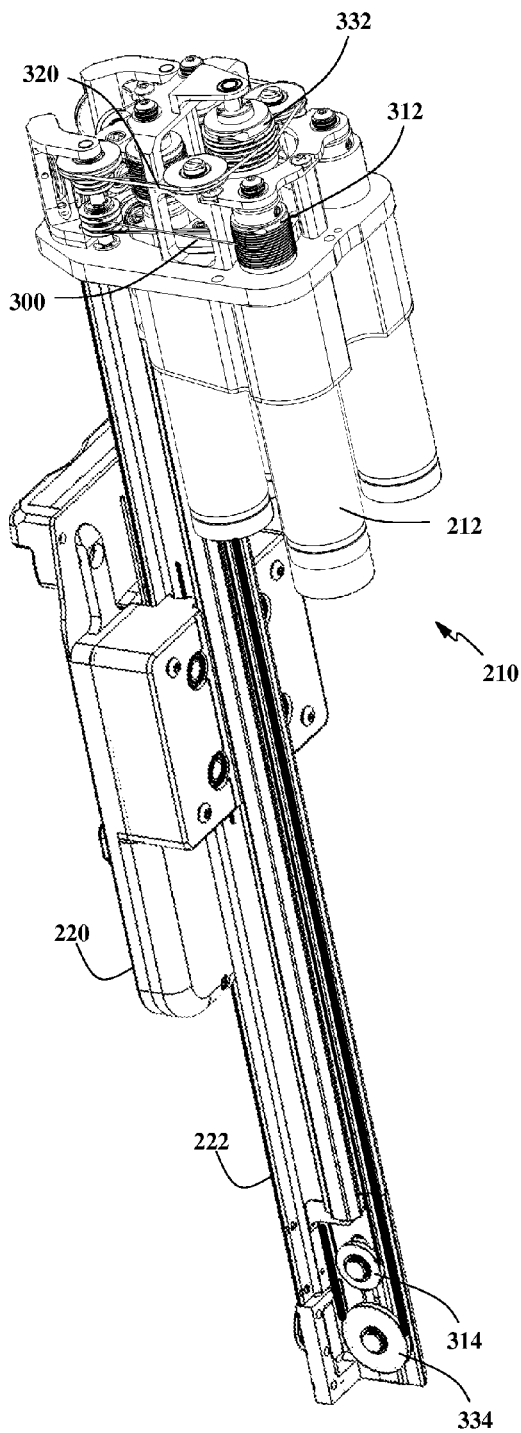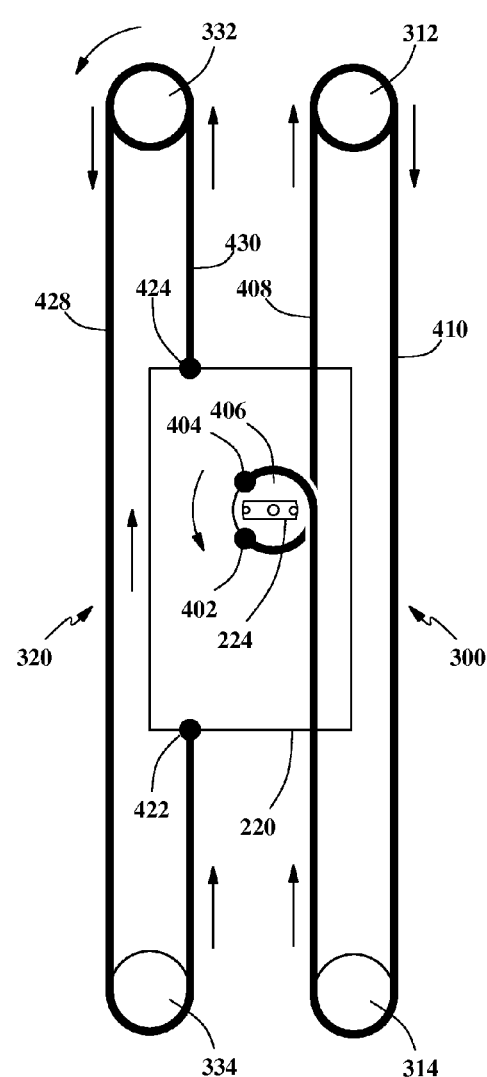
FIG. 3
FIG. 4

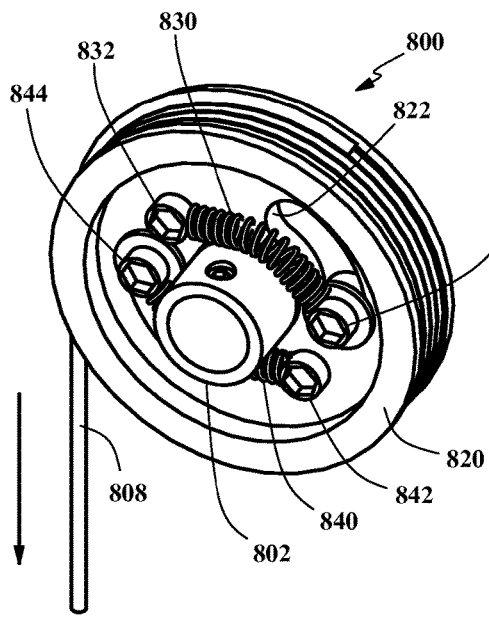
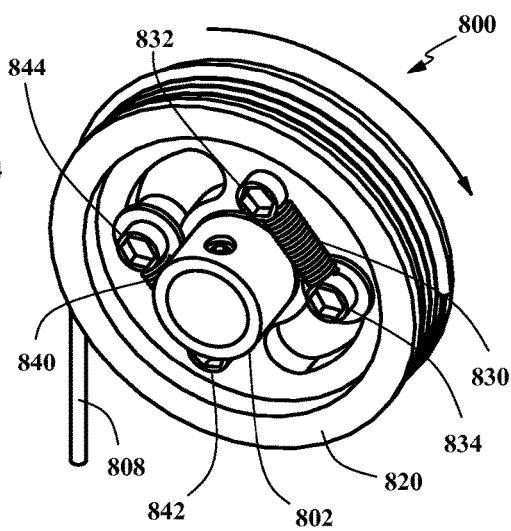
FIG. 8A  FIG. 8B
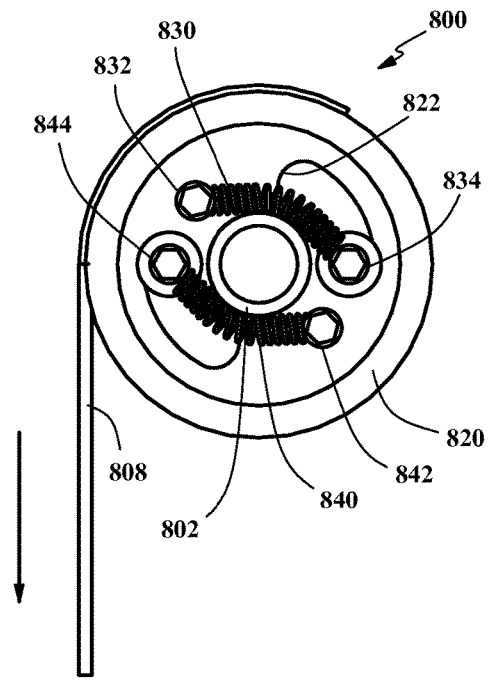
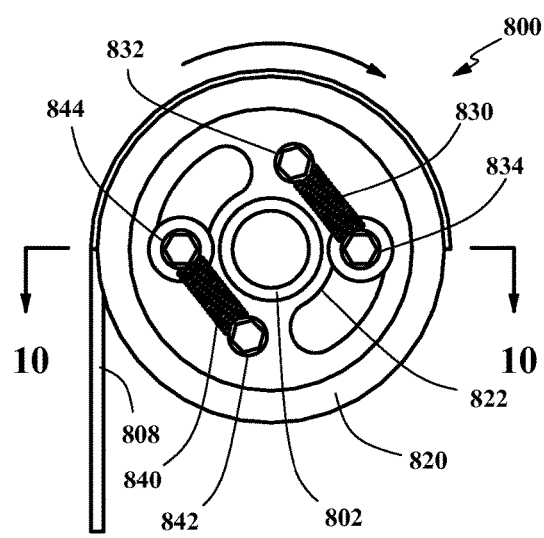
FIG. 9A  FIG. 9B

COMPACT CABLE TENSION TENDER DEVICE

CROSS REFERENCE TO RELATED APPLICATIONS

This application is a continuation of application Ser. No. 11/549,087, filed Oct. 12, 2006, which is hereby incorporated by reference in its entirety.

BACKGROUND

Minimally invasive surgery (MIS) provides surgical techniques for operating on a patient through small incisions using a camera and elongate surgical instruments introduced to an internal surgical site, often through trocar sleeves or cannulas. The surgical site often comprises a body cavity, such as the patient's abdomen. The body cavity may optionally be distended using a clear fluid such as an insufflation gas. In traditional minimally invasive surgery, the surgeon manipulates the tissues using end effectors of the elongate surgical instruments by actuating the instrument's handles while viewing the surgical site on a video monitor.

A common form of minimally invasive surgery is endoscopy. Laparoscopy is a type of endoscopy for performing minimally invasive inspection and surgery inside the abdominal cavity. In standard laparoscopic surgery, a patient's abdomen is insufflated with gas, and cannula sleeves are passed through small (generally ½ inch or less) incisions to provide entry ports for laparoscopic surgical instruments. The laparoscopic surgical instruments generally include a laparoscope (for viewing the surgical field) and instruments for performing surgical functions such as gripping or cutting.

Laparoscopic surgical instruments are similar to those used in conventional (open) surgery, except that the working end or end effector of each instrument is separated from its handle by a shaft. As used herein, the term "end effector" means the actual working part of the surgical instrument and can include clamps, graspers, scissors, staplers, image capture lenses, and needle holders, for example. To perform surgical procedures, the surgeon passes these surgical instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in other types of surgeries such as arthroscopy, retroperitoneoscopy, pelviscopy, nephroscopy, cystoscopy, cisternoscopy, sinoscopy, hysteroscopy, urethroscopy, and the like.

Robotic control may provide an improved control interface to the surgeon. Robotically controlled surgical instruments may be driven by servo mechanisms, such as servo motors, that are coupled to the surgical instrument by mechanical cables. Each servo mechanism may be coupled to a cable by a driving pulley that draws in and pays out the cable wound around the driving pulley. The cable may be routed to and from the driving pulley by one or more guide pulleys. As space in the surgical field over a patient where robotically controlled surgical instruments are being used is at a premium, it is desirable to have a compact mechanism to drive and control the robotically controlled surgical instruments.

The cable may rotate a driven pulley that is coupled to the robotically controlled surgical instrument to drive and control movement of the instrument. A portion of the cable may be wound around the driving and/or driven pulley more than once to improve the transfer of force and motion between the cable and the pulley. The cable may be made up of two or more cable segments. The ends of segments may be attached to pulleys and these segment ends may be wound around the driving and/or driven pulley more than once to provide a larger range of motion. The driving and driven pulleys may be referred to as capstans in such configurations.

The cable may move a linearly driven mechanism, such as a carriage, rather than rotate a driven pulley. While the description will primarily discuss systems with a rotationally driven pulley, it should be understood that in many, but not all of the systems, a linearly driven mechanism may be substituted for the rotationally driven pulley.

The cable may be split at the driving and/or driven pulley with each of the cable segment ends coupled to the pulley to provide a positive connection between the cable and the pulley. It will be appreciated that the two cable segments will still continue to function as they would if the cable was wound around the pulley as a single continuous cable. References to a cable should be understood to include arrangements of two or more cable segments where the segments are operatively coupled, such as by being joined to a pulley that transfers force and motion from one segment to the other.

In a typical cable drive system for a robotically controlled surgical instrument, a cable is guided by a pulley and wound onto a pulley that is fixed to a shaft that is driven by a motor. The cable is normally adjusted to place the cable in tension. Maintaining tension in the cable may be necessary to keep the cable properly positioned on the guiding pulleys and the driving and driven pulleys.

The cable may stretch under an applied load. The stretch may be constructional and/or elastic. Constructional stretch is the result of the clearances between the individual wires and strands being reduced as the cable is loaded, allowing the cable to "stretch" in length. Elastic stretch is the actual elongation of the individual wires in a strand or cable when subjected to a load that is less than the yield point of the metal. When the load is removed from the cable it will return to its original length.

A cable can only transmit force or motion in tension. Thus the applied force must draw in the cable and pull on the driven end. In a system that uses a cable loop between the driving pulley and the driven pulley, one portion of the cable will be drawn in by the driving pulley. The tension in the drawn in portion of the cable may be increased substantially if the driven end is working against mechanical resistance. The increase in tension may cause this portion of the cable to stretch.

The other portion of the cable in a cable loop is payed out by the driving pulley and taken up by the driven pulley. The tension in the payed out portion of the cable may be reduced substantially, or even eliminated, if the driven end is working against mechanical resistance. Further, if the drawn in portion of the cable stretches, the increased length of the cable will also contribute to slack in the payed out portion of the cable.

It may be necessary to provide a mechanism to maintain tension in the payed out portion of the cable to keep the cable loop properly positioned. This may be accomplished by including an extension spring as part of the cable. However this requires that there be a portion of the cable with a distance between pulleys that is greater than the range of motion of the cable. A distance between the pulleys is necessary because the extension spring is normally substantially larger in diameter than the cable and thus cannot pass over the pulleys. Including an extension spring as part of the cable may be detrimental if the cable loop is required to provide positive force and/or positioning in both directions. Including an in-line spring as part of the cable loop may greatly increase the elasticity of the cable loop and adversely affect the ability to positively transmit force and/or motion between the driving pulley and the driven pulley.

It would be desirable to provide a mechanism that can compensate for stretching of a cable loop with positive transmission of force and/or motion without requiring additional space between pulleys.

SUMMARY

A compact cable tension tender device includes a movable member having a first stop and a second stop spaced apart from the first stop. A first attachment may be provided on the moveable member for cable that extends in a first direction. The first attachment may engage the first stop to limit the movement of the cable in the first direction relative to the movable member. A second attachment may be provided on the moveable member for cable that extends in a second direction. The second attachment may engage the second stop to limit the movement of the cable in the second direction relative to the movable member. A resilient coupler coupled to the first attachment and to the second attachment may urge the first attachment to move in the second direction and the second attachment to move in the first direction relative to each other to maintain cable tension.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIG. 1 is a pictorial view of a robotic surgical tool that includes an embodiment of the invention.

FIG. 2 is a side view of a robotic surgical tool that includes an embodiment of the invention.

FIG. 3 is a pictorial view of a robotic surgical tool that includes an embodiment of the invention.

FIG. 4 is a schematic view of the robotic surgical tool of FIG. 3.

FIGS. 8A and 8B are pictorials view of another device that embodies the invention shown in two operative positions.

FIGS. 9A and 9B are end views of the device shown in FIGS. 8A and 8B.

DETAILED DESCRIPTION

Figure 5:
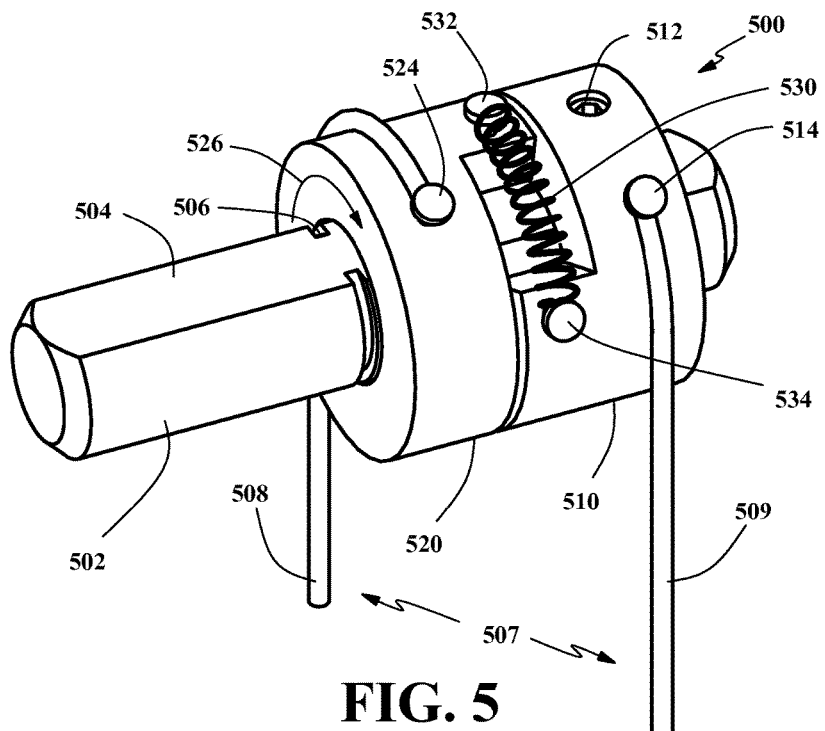
FIG. 5 is a pictorial view of a device that embodies the invention.

Endoscopy may be performed with robotically controlled surgical instruments, such as the one shown in FIGS. 1-3. A robotic arm 102 may support and position a robotic surgical instrument 104. The surgical instrument 104 may have a head portion 200 that is coupled to a movable carriage 220 on the robotic arm 102. A spar 222 may provide a linear track for the movable carriage 220, allowing the robotic arm to change the depth of insertion of the surgical instrument 104 by moving the carriage along the spar.

The robotic arm 102 may include one or more servo motors 212 that are coupled to the movable carriage 220 to robotically move the surgical instrument 104. Each servo motor 212 may be coupled to the movable carriage by a cable loop as may be seen in FIG. 3 and represented schematically in FIG. 4.

One servo motor 212 may drive a pulley 332 that is coupled to the movable carriage 220 by a cable loop 320 to move the carriage along the spar 222 under the control of the servo motor. To move the carriage 220, one segment 430 of the cable loop 320 is drawn in by the servo motor 212 driven pulley 332 while a second cable segment 428 is payed out. A guide pulley 334 may be provided to change the direction of the cable 320 as required. It will be appreciated that only the segment 430 of the cable loop 320 being drawn in by the pulley 332 provides motive force to the movable carriage 220.

Another servo motor 212 may drive a pulley 312 that is coupled to a rotatable driver 224 on the movable carriage 220 by a cable loop 300 to rotate the driver under the control of the servo motor. The driver 224 may be coupled to the head 200 (FIG. 1) of the surgical instrument 104 to control the motion of an end effector 204 that may be located at the end of a shaft 202 connected to the head. To move the driver 224, one segment 408 of the cable loop 300 is drawn in by the servo motor 212 driven pulley 312 while a second segment 410 is payed out. A guide pulley 314 may be provided to change the direction of the cable 300 as required. It will be appreciated that only the segment 410 of the cable loop 300 being drawn in by the servo motor 212 driven pulley 312 provides motive force to the driver 224.

Figures 6, 7:
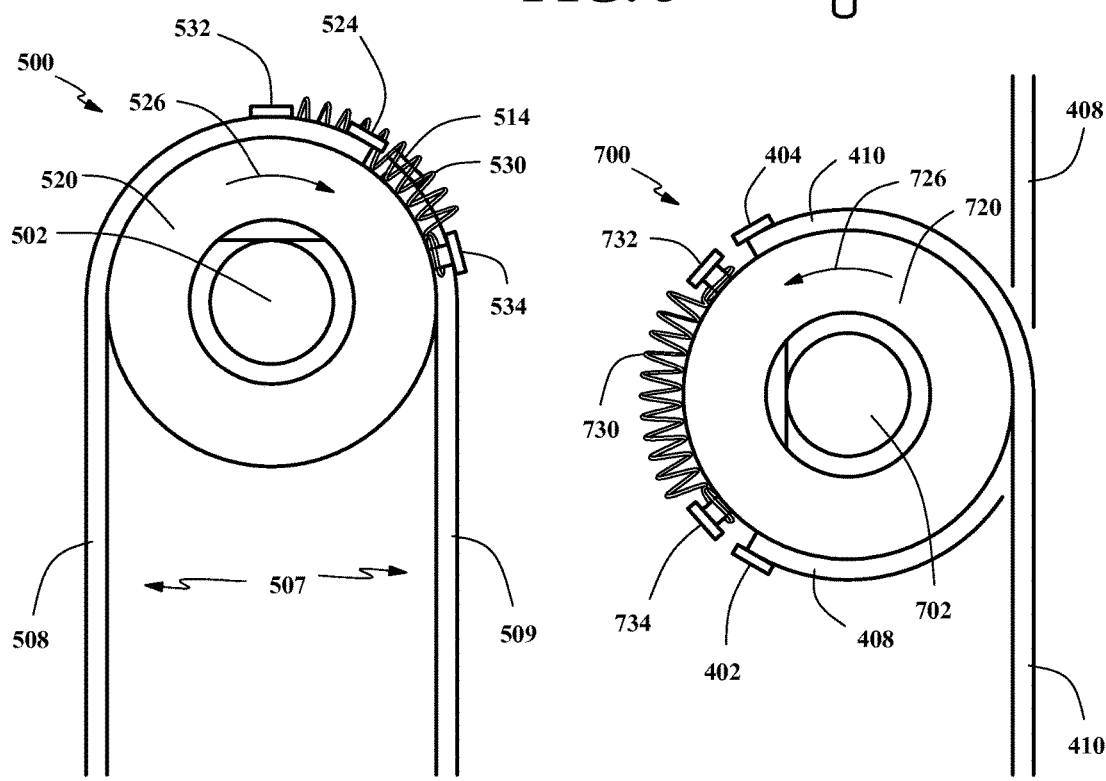
FIG. 6 is an end view of the device of FIG. 5.
FIG. 7 is an end view of another device that embodies the invention.

FIGS. 5 and 6 show a tension tender device 500 that may be coupled to a servo motor 412, 432 or a rotatable driver 224 to couple a cable loop 507 to the servo motor or rotatable driver. The tension tender device 500 may include a drive shaft 502 and a first pulley 510 that is coupled to the drive shaft. The first pulley 510 may be fixed to rotate in unison with the drive shaft 502. For example, the first pulley 510 may be fixed to a flat 504 on the drive shaft 502 by a set screw 512 in the first pulley. In other embodiments, the first pulley and the drive shaft may be a single part or may be joined by other means such as a roll pin, a key and slot, splines, or a press fit. The first pulley 510 may provide an attachment 514 for an end of a segment 509 of the cable 507.

The tension tender device 500 may include a second pulley 520 rotatably coupled to the drive shaft 502. The second pulley 520 may be constrained axially on the drive shaft 502, such as by the first pulley 510 and a snap ring (not shown) installed in a groove 506 in the drive shaft 502. The second pulley 520 may provide an attachment 524 for an end of a second segment 508 of the cable 507.

A resilient coupler 530, such as an extension spring, may couple an attachment 532 on the second pulley 520 to the drive shaft 502. In the tension tender device 500 illustrated in FIG. 5, the resilient coupler 530 is coupled to the drive shaft 502 through an attachment 534 on the first pulley 510 which is fixed to the drive shaft. The resilient coupler 530 urges the second pulley 520 to rotate relative to the drive shaft 502. Referring to FIG. 5 and to the left end view in FIG. 6 for example, the resilient coupler 530 urges the second pulley 520 to rotate clockwise as suggested by the arrow 526 shown on the face of the second pulley 520.

If the tension tender 500 shown in FIGS. 5 and 6 is used as the pulley 332 shown in FIG. 4, the cable segment 509 fixed to the drive shaft 502 corresponds to cable segment 430 that provides the motive force to the carriage 220. The cable segment 428 being payed out corresponds to the cable segment 508 that is attached to the second pulley 520, which can be drawn onto the second pulley by the resilient coupler 530 if slack develops in the portion of the cable 320 being payed out.

FIG. 7 is an end view of a tension tender 700 having a similar construction to the tension tender 500 shown in FIGS. 5 and 6 and as may be applied to the driver 224 as shown in FIG. 4. It will be appreciated that this tension tender 700 operates in the opposite direction from the embodiment shown in FIGS. 5 and 6. The tension tender device 700 may be coupled to the rotatable driver 224 to couple the cable loop 400 to the rotatable driver as shown schematically in FIG. 4. The first cable end 408 of the cable 400 is drawn off of the driver 224 to rotate the driver counter-clockwise. The second end 410 of the cable 400 is drawn on to the driver 224.

It will be appreciated that the servo motor 312 will increase the tension force in the first segment 408 of the cable 400 to rotate the driver 224 in the counter-clockwise direction indicated by the arrow. The tension in the second segment 410 of the cable 400 will be reduced by this action. It is possible that the second segment 410 of the cable 400 could go slack, particularly if the driver 224 is heavily loaded such as by encountering a solid obstacle. However, the resilient coupler 730 will cause the second pulley 720 rotate clockwise relative to the drive shaft 702 as suggested by the arrow 726 on the face of the second pulley. This may maintain tension in the second segment 410 of the cable 400 when tension is not applied to that segment of the cable.

The tension tender device 500 may coupled to the servo motor 432 to couple the cable loop 420 to the moving carriage 220 as shown schematically in FIG. 4. The motor 432 may be coupled to the drive shaft 502 to rotate the drive shaft in a counter-clockwise direction as suggested by the arrow in FIG. 4. The first cable end 509 shown in FIG. 5 would correspond to the first segment 430 of the cable 420 pulling the carriage 220 toward the servo motor 432 in FIG. 4. The second cable end 508 shown in FIG. 5 would correspond to the second segment 428 of the cable 400 being drawn out by the carriage 220 in FIG. 4.

It will be appreciated that the servo motor 432 will increase the tension force in the first segment 430 of the cable 420 to pull the carriage 220. The tension in the second segment 428 of the cable 420 will be reduced by this action. It is possible that the second segment 428 of the cable 420 could go slack, particularly if the carriage 220 is heavily loaded such as by encountering a solid obstacle. However, the resilient coupler 530 will cause the second pulley 520 rotate clockwise relative to the drive shaft 502 as suggested by the arrow 526 on the face of the second pulley. This may maintain tension in the second segment 428 of the cable 420 when tension is not applied to that segment of the cable.

FIGS. 8 to 11 show another embodiment of a tension tender device 800. The tension tender device 800 may include a drive shaft 802 and a pulley 820 that is rotatably coupled to the drive shaft 802. The drive shaft 802 may be in the form of a hub with a through bore to allow the tension tender device 800 to be mounted to another shaft to functionally extend the drive shaft 802 of the tension tender device.

Figure 10:
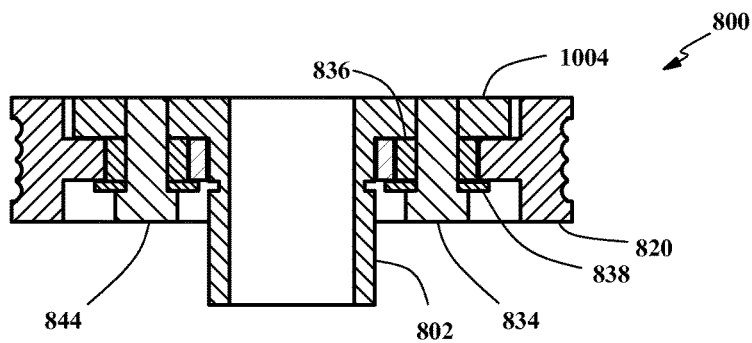
FIG. 10 is a cross-sectional view of the device taken on section line 10-10 in FIG. 9B.

As best seen in the cross section of FIG. 10, the pulley 820 is rotatably held on the drive shaft 802. The pulley 820 may be axially constrained. For example, the drive shaft 802 may include a flange 1004 that constrains the pulley 820 in one axial direction. A stop assembly may be formed from a screw 834, a bushing 836, and a washer 838 that is fixed to the flange 1004 of the drive shaft 802. The stop assembly may pass through a slotted opening in the face of the pulley 820. The washer 838 portion of the stop assembly may constrain the pulley 820 in a second axial direction. It will be appreciated that the pulley 820 may be axially constrained by means other than the stop assembly.

A resilient coupler 830, such as an extension spring, may couple an attachment 832 on the pulley 820 to the drive shaft 802. In the tension tender device 800 illustrated in FIG. 8, the resilient coupler 830 is coupled to the drive shaft 802 through the stop assembly which is fixed to the drive shaft. The resilient coupler 530 urges the pulley 820 to rotate relative to the drive shaft 802.

Figure 11:
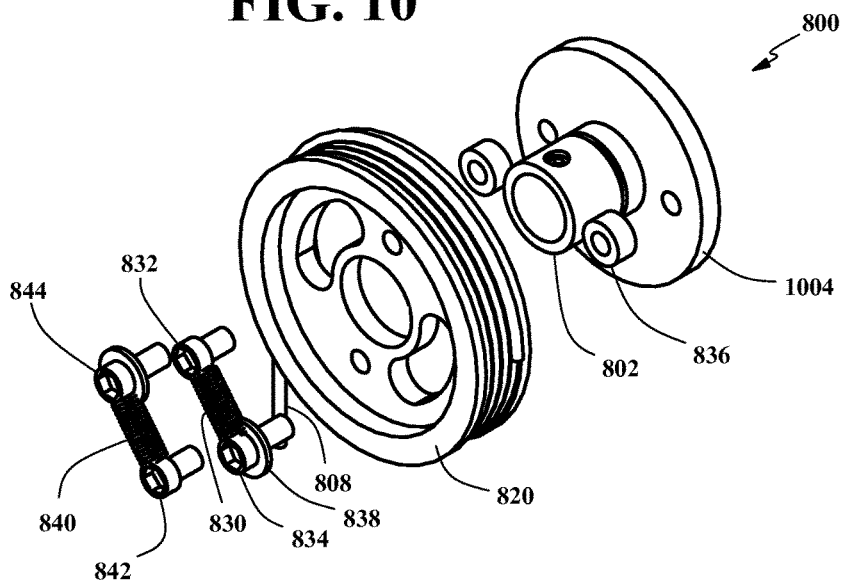
FIG. 11 is an exploded view of the device shown in FIG. 8B.

One or both faces of the pulley 820 may include a recessed portion to receive one or more of the flange 1004, the stop assembly, and the resilient coupler 830. This may contribute to the compactness of the tension tender device 800. FIG. 11 shows the parts in an exploded view.

Referring to FIGS. 8A and 8B and to the left end views in FIGS. 9A and 9B for example, the resilient coupler 830 urges the pulley 820 to rotate clockwise. FIGS. 8A and 9A show the pulley 820 in a first position where tension is applied to a cable segment 808 that is attached to the pulley. FIGS. 8B and 9B show the pulley 820 in a second position where the cable segment 808 has gone slack. As suggested by the arrow 826, the resilient coupler 830 has caused the pulley 820 to rotate clockwise relative to the drive shaft 802 and take up the slack in the attached cable segment 808.

When tension is applied to a cable segment 808 that is attached to the pulley 820 as shown in FIGS. 8A and 9A, the pulley may rotate against the force of the resilient coupler 830 and cause the stop assembly to engage the pulley. For example, the bushing 836 may engage the end of the slot 822. When the stop assembly engages the pulley 820, the pulley will operate as though it were fixed to the drive shaft 802. Tension in the attached cable segment 808 will be positively coupled to rotation of the drive shaft.

When tension is applied to the attached cable segment 808, the pulley 820 of this embodiment acts in the same manner as the first pulley 510 of the embodiment of a tension tender device 500 shown in FIG. 5. When the attached cable segment 808 goes slack, the pulley 820 of this embodiment acts in the same manner as the second pulley 520 of the embodiment shown in FIG. 5.

Figure 12:
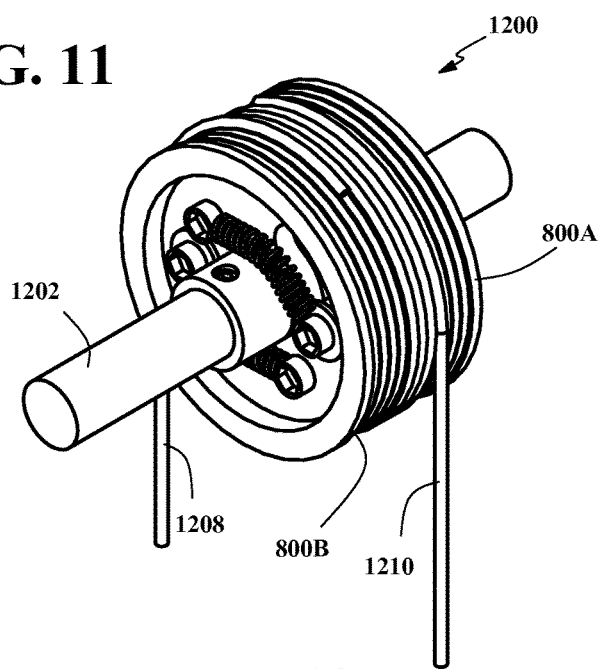
FIG. 12 is a pictorial view of another device that embodies the invention.

As shown in FIG. 12, two tension tender devices 800A, 800B of the type shown in FIGS. 8 to 11 may be assembled back to back on a supporting drive shaft 1202. This assembly 1200 will operate to positively couple whichever of the attached cable segments 1208, 1210 is in tension to the drive shaft 1202. If the remaining cable segment 1208, 1210 goes slack, the resilient coupler 830 of the tension tender device 800A, 800B to which the slack cable segment is attached will cause the pulley 820 to rotate relative to the drive shaft 1202 to maintain tension in the cable. It may be advantageous to adjust the system so that both attached cable segments 1208, 1210 are in tension such that both stop assemblies engage their respective pulleys. This may minimize lost motion when reversing the direction of motion.

Figure 13:
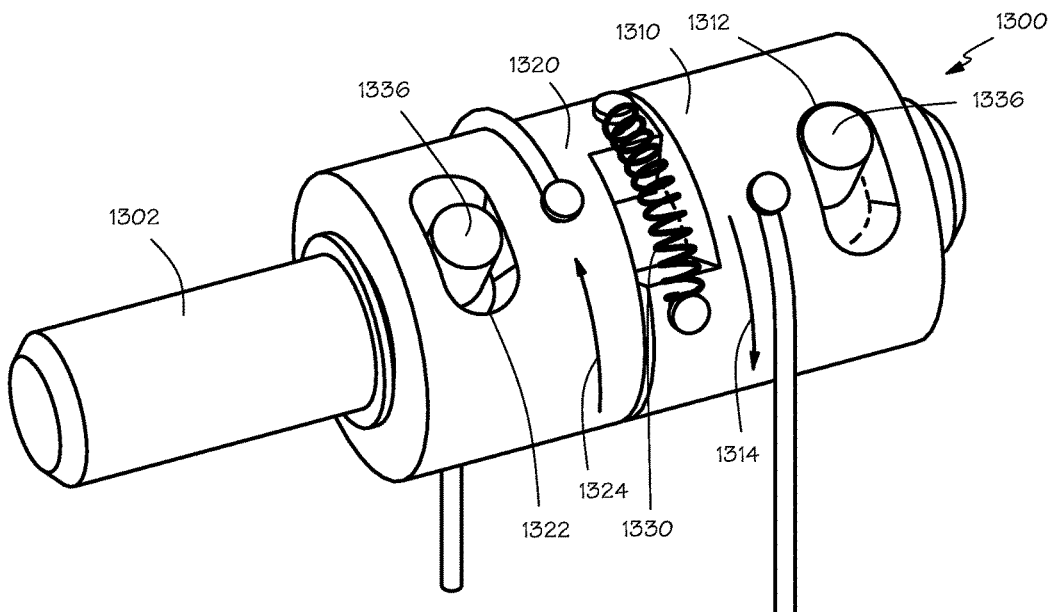
FIG. 13 is a pictorial view of another device that embodies the invention.

FIG. 13 shows another embodiment of a tension tender device 1300. In this embodiment, the drive shaft 1302 includes drive stops in the form of pins 1336 that extend radially though the drive shaft. Two pulleys 1310, 1320 are rotatably coupled to the drive shaft 1302. The first pulley 1310 includes a first stop 1312 that engages the drive stop 1336 when the first pulley is rotated in a first direction 1314. The second pulley 1320 includes a second stop 1322 that engages the drive stop 1336 when the second pulley is rotated in a second direction 1324.

A resilient coupler 1330 is coupled to the first pulley 1310 and to the second pulley 1320. The resilient coupler 1330 urges the second pulley 1320 to rotate in the first direction when the first stop 1312 of the first pulley 1310 engages the drive stop 1336. The resilient coupler 1330 urges the first pulley 1310 to rotate in the second direction when the second stop 1322 of the second pulley 1320 engages the drive stop 1336. This configuration may allow a single spring to be used as the resilient coupler 1330 for a tension tender device 1300 that maintains cable tension in both directions of motion.

Figure 15:
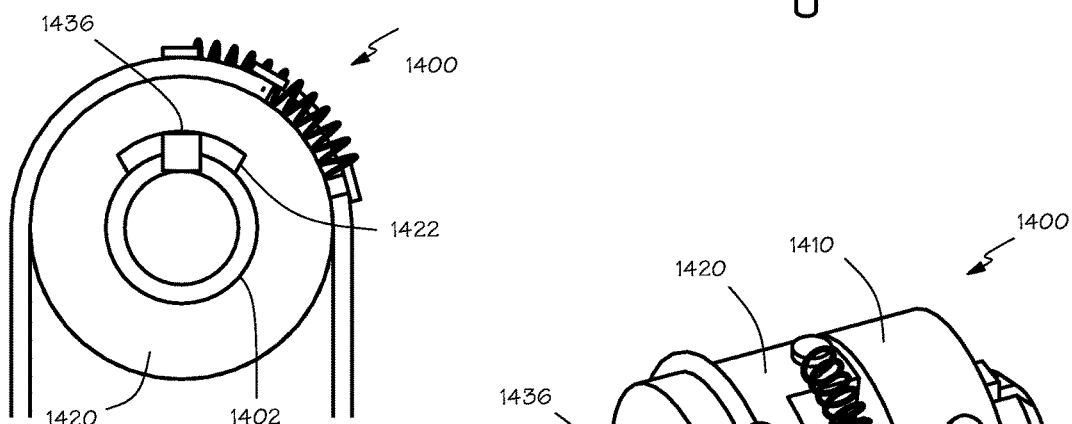
FIG. 15 is an end view of the device of FIG. 14.
Figure 14:
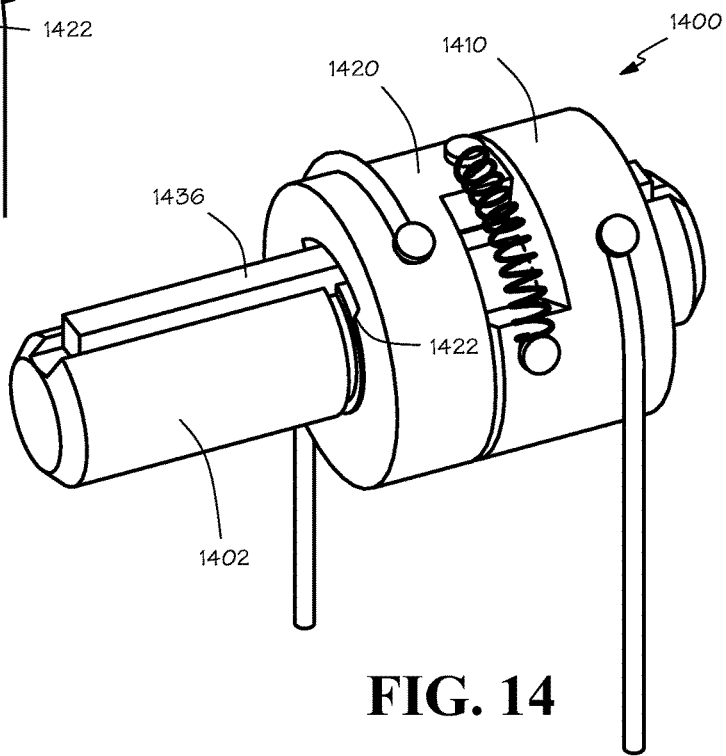
FIG. 14 is a pictorial view of another device that embodies the invention.

FIGS. 14 and 15 show another embodiment of a tension tender device 1400. In this embodiment, the drive shaft 1402 includes drive stops in the form of a key 1436 that extend axially along the drive shaft. The pulleys 1410, 1420 include stops in the form of a wide keyway that allows a limited range of rotation. As seen in the left end view of FIG. 15, the second pulley 1420 includes a second stop 1422 that engages the drive stop 1436 when the second pulley is rotated counter-clockwise.

Figures 16A, 16B:
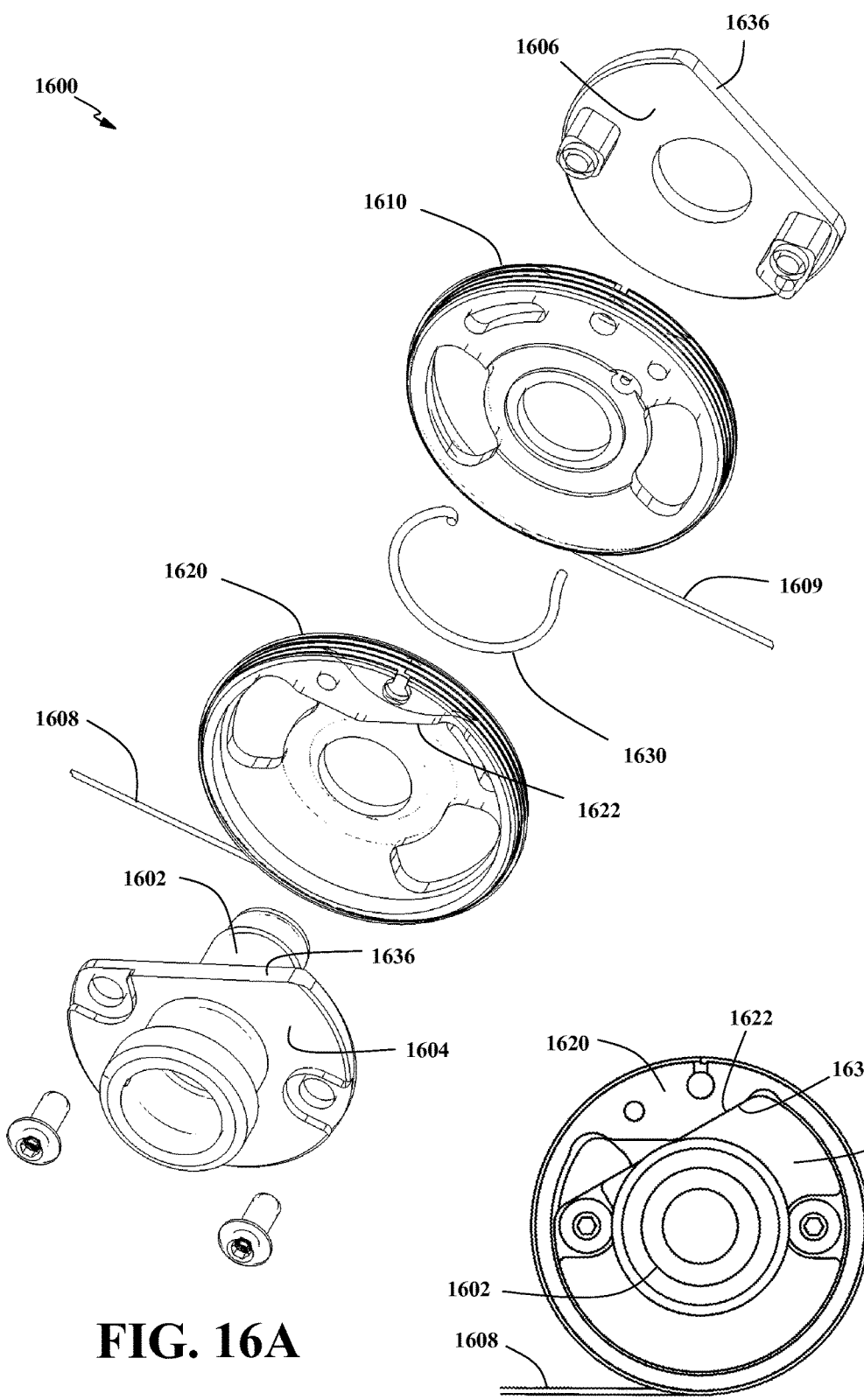
FIG. 16A is an exploded view of another device that embodies the invention.
FIG. 16B is an end view of a portion of the device of FIG. 16A.

FIGS. 16A and 16B show another embodiment of a tension tender device 1600. In this embodiment, the drive shaft 1602 includes a first plate 1604 that provides a first axial constraint for the pulleys 1610, 1620. The first plate 1604 is coupled to a second plate 1606 that provides a second axial constraint for the pulleys 1610, 1620.

Each of the two plates 1604, 1606 includes a drive stop 1636 in the form of a flat edge on the plate. Each of the two pulleys 1610, 1620 includes a stop 1622 in the form of a recess that includes a flat edge. As best seen in FIG. 16B, an end view of one pulley 1620, the drive stop 1636 on the plate engages the stop 1622 on the pulley when the cable segment 1608 that is attached to the pulley is in tension.

If the cable segment 1608 that is coupled to the pulley 1620 is drawn off the pulley to rotate the pulley clockwise, the pulley will rotate relative to the drive shaft 1602 until the stop 1622 on the pulley engages the drive stop 1636 that is coupled to the drive shaft. The drawing of the cable segment 1608 will then positively rotate the drive shaft 1602 clockwise. If the second cable segment 1609 coupled to the second pulley 1610 goes slack, the resilient coupler 1630 will rotate the second pulley in a clockwise direction, causing the stop 1622 on the second pulley to separate from the drive stop 1636 and maintain tension in the second cable segment.

If the drive shaft 1602 is rotated counter-clockwise, such as by a motor, the drive shaft will rotate relative to the pulley 1620 until the drive stop 1636 that is coupled to the drive shaft engages the stop 1622 on the pulley. The rotation of the drive shaft 1602 will then positively rotate the pulley 1620 counter-clockwise to wind in the cable segment 1608. If the second cable segment 1609 coupled to the second pulley 1610 goes slack, the resilient coupler 1630 will rotate the second pulley in a clockwise direction, causing the stop 1622 on the second pulley to separate from the drive stop 1636 and maintain tension in the second cable segment.

It will be appreciated that the stop assembly 1622, 1636 of the second pulley 1610 and the second plate 1606 will operate as described for the first pulley 1620 and the first plate 1604 for motion in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A tension tender device comprising:
    a drive shaft;
    a first plate fixedly coupled to the drive shaft and including a first drive stop;
    a first pulley rotatably coupled to the drive shaft, the first pulley including a first recess that receives the first plate;
    a first cable coupled to the first pulley, the first cable rotating the first pulley in a first direction when the first cable is in tension and thereby causing the first recess in the first pulley to engage the first drive stop; and
    a resilient coupler coupled to the first pulley, the resilient coupler to urge the first pulley to rotate in a second direction opposite the first direction whenever the first cable is not in tension.

2. The tension tender device of claim 1 wherein the first drive stop is a surface on the periphery of the first plate that is parallel to an axis of rotation of the drive shaft.

3. The tension tender device of claim 1 further comprising a motor coupled to the drive shaft, the motor to rotate the drive shaft in the second direction to cause the drive stop to positively rotate the first pulley in the second direction and wind in the first cable.

4. A tension tender device comprising:
    a drive shaft;
    a first plate fixedly coupled to the drive shaft and including a first drive stop;
    a first pulley rotatably coupled to the drive shaft, the first pulley including a first recess that receives the first plate;
    a second plate fixedly coupled to the drive shaft and including a second drive stop;
    a second pulley rotatably coupled to the drive shaft, the second pulley including a second recess that receives the second plate;
    a first cable coupled to the first pulley, the first cable rotating the first pulley in a first direction when the first cable is in tension and thereby causing the first recess in the first pulley to engage the first drive stop;
    a second cable coupled to the second pulley, the second cable rotating the second pulley in a second direction opposite the first direction when the second cable is in tension and thereby causing the second recess in the second pulley to engage the second drive stop independently of the first recess in the first pulley engaging the first drive stop; and
    a resilient coupler coupled to the first and second pulleys, the resilient coupler urging the first pulley to rotate in the second direction whenever the first cable is not in tension and urging the second pulley to rotate in the first direction whenever the second cable is not in tension.

5. The tension tender device of claim 4 further comprising a motor coupled to the drive shaft, the motor to rotate the drive shaft in the second direction to cause the first drive stop to positively rotate the first pulley in the second direction and wind in the first cable and to rotate the drive shaft in the first direction to cause the second drive stop to positively rotate the second pulley in the first direction and wind in the second cable, wherein the engagement of the first pulley and the first drive stop together with the engagement of the second pulley and the second drive stop minimizes lost motion when reversing the rotation of the drive shaft.

6. The tension tender device of claim 4 wherein the first and second drive stops are surfaces on the periphery of the first and second plates that are parallel to the axis of rotation of the drive shaft.

7. The tension tender device of claim 4 wherein the first and second recesses face away from each other and the first and second plates rotatably couple the first and second pulleys to the drive shaft.

8. A tension tender device comprising:
a drive shaft;
a first drive stop fixedly coupled to the drive shaft;
a second drive stop fixedly coupled to the drive shaft;
a first pulley rotatably coupled to the drive shaft, the first pulley including a first stop surface that is fixed to the first pulley;
a second pulley rotatably coupled to the drive shaft, the second pulley including a second stop surface that is fixed to the second pulley;
a first cable coupled to the first pulley, the first cable rotating the first pulley in a first direction when the first cable is in tension and thereby causing the first stop surface of the first pulley to engage the first drive stop;
a second cable coupled to the second pulley, the second cable rotating the second pulley in a second direction when the second cable is in tension and thereby causing the second stop surface of the second pulley to engage the second drive stop independently of the first stop surface of the first pulley engaging the first drive stop; and
means for urging the first pulley to rotate in the second direction whenever the first cable is not in tension and for urging the second pulley to rotate in the first direction whenever the second cable is not in tension.

9. The tension tender device of claim 8 further comprising means for rotating the drive shaft in the second direction to positively rotate the first pulley in the second direction and wind in the first cable and for rotating the drive shaft in the first direction to cause the second drive stop to positively rotate the second pulley in the first direction and wind in the second cable, wherein the engagement of the first stop surface and the first drive stop together with the engagement of the second stop surface and the second drive stop minimizes lost motion when reversing the rotation of the drive shaft.

10. The tension tender device of claim 8 wherein the first drive stop and the second drive stop retain the first and second pulleys on the drive shaft.

11. A method of driving a cable loop, the method comprising:
coupling a first cable to a first pulley that includes a first stop surface that is fixed to the first pulley;
coupling a second cable to a second pulley that includes a second stop surface that is fixed to the second pulley;
adjusting the first cable to rotate the first pulley in a first direction and cause the first stop surface to engage a first drive stop fixed to a drive shaft;
adjusting the second cable to rotate the second pulley in a second direction opposite the first direction and cause the second stop surface to engage a second drive stop fixed to the drive shaft independently of the first stop surface engaging the first drive stop;
coupling the first pulley to the second pulley with a resilient coupler that urges the first pulley to rotate in the second direction whenever the first cable is not in tension and that urges the second pulley to rotate in the first direction whenever the second cable is not in tension;
rotating the drive shaft in the second direction to drive the cable loop by applying tension to the first cable; and
rotating the drive shaft in the first direction to drive the cable loop by applying tension to the second cable, wherein the engagement of the first stop surface and the first drive stop together with the engagement of the second stop surface and the second drive stop minimizes lost motion when reversing the rotation of the drive shaft.

12. The method of claim 11, wherein adjusting the first cable puts the first cable in tension and adjusting the second cable puts the second cable in tension.

13. The method of claim 11, wherein the drive shaft, the first pulley, and the second pulley are rotated about a common axis.

* * * * *